United States Patent [19]

Reuschling et al.

[11] 4,066,690

[45] Jan. 3, 1978

[54] PROCESS FOR THE PREPARING α-CHLOROACRYLIC ACID CHLORIDES

[75] Inventors: Dieter-Bernd Reuschling, Butzbach; Harald Jensen, Frankfurt am Main, both of Germany

[73] Assignee: Hoechst Aktiengesellschaft, Frankfurt am Main, Germany

[21] Appl. No.: 724,959

[22] Filed: Sept. 20, 1976

Related U.S. Application Data

[63] Continuation-in-part of Ser. No. 524,811, Nov. 18, 1974, abandoned.

[30] Foreign Application Priority Data

July 24, 1975   Germany .............................. 2357677

[51] Int. Cl.² ............................................. C07C 51/58
[52] U.S. Cl. .................................................. 260/544 Y
[58] Field of Search .................................... 260/544 Y

[56] References Cited

U.S. PATENT DOCUMENTS

| 2,050,752 | 8/1936 | Fikentscher | 260/544 Y |
|---|---|---|---|
| 2,388,657 | 11/1945 | Long | 260/544 Y |
| 2,396,609 | 3/1946 | Schmidt | 260/544 Y |
| 2,862,960 | 12/1958 | Pollack | 260/544 Y |
| 2,870,193 | 1/1959 | Pollack | 260/544 Y |
| 3,395,174 | 7/1968 | Knell et al. | 260/544 Y |
| 3,940,439 | 2/1976 | Harrow | 260/544 Y |

FOREIGN PATENT DOCUMENTS

| 822,369 | 5/1975 | Belgium | 260/544 Y |
|---|---|---|---|
| 7,414,878 | 5/1975 | France | 260/544 Y |
| 2,357,677 | 7/1975 | Germany | 260/544 Y |
| 2,251,541 | 6/1975 | Netherlands | 260/544 Y |
| 563,047 | 7/1944 | United Kingdom | 260/544 Y |

*Primary Examiner*—Norman Morgenstern
*Attorney, Agent, or Firm*—Curtis, Morris & Safford

[57] ABSTRACT

α-Chloroacrylic acid chloride is obtained in a high yield by splitting off HCl from α,β-dichloropropionic acid chloride at an increased temperature and under reduced pressure in the presence of a tertiary phosphine, a quaternary phosphonium salt or a tertiary phosphine oxide, sulfide, halide or imine. α-Chloroacrylic acid chloride is important as a starting and intermediate material for further syntheses, especially as the starting material for the total synthesis of prostaglandins according to Corey.

16 Claims, No Drawings

PROCESS FOR THE PREPARING α-CHLOROACRYLIC ACID CHLORIDES

This application is a continuation-in-part of application Ser. No. 524,811, filed Nov. 18, 1974 now abandoned.

The present invention relates to a process for preparing α-chloroacrylic acid chloride, a highly active dienophile and an important starting material for the total synthesis of prostaglandins according to Corey.

Processes for preparing α-chloroacrylic acid chlorides from α-chloroacrylic acid are already known.

α-Chloroacrylic acid chloride may be obtained for example from reaction of α-chloracrylic acid and benzoyl chloride, in the presence of antimony (V) chloride or copper (I) chloride, in a yield of from 17 to 39%.

According to another process the acid chloride is produced in a yield of 38% by reaction of α-chloroacrylic acid with thionyl chloride in the presence of copper (I) chloride and sodium methylate.

In a further process, α-chloroacrylic acid is initially reacted with phosgene at a temperature of 40° C in the presence of dimethyl formamide. The α,β-dichloropropionic acid chloride formed in this process is dissociated thereafter into α-chloroacrylic acid chloride (yield of crude product 89%) and hydrogen chloride, under reduced pressure at a temperature of from 100° to 150° C.

In another process, disclosed in *J. Am. Chem. Soc.*, Vol. 62, at 3495 (1940), α,β-dichloropropionic acid chloride is dehydrochlorinated with diethyl aniline at 85° C under reduced pressure to give α-chloroacrylic acid chloride in a moderate yield of 37%.

All processes previously known have a number of attendant disadvantages.

The use of α-chloroacrylic acid requires considerable technical expenditure because said acid can only be produced by complicated methods. Owing to the fact that α-chloroacrylic acid as well as α-chloroacrylic acid chloride easily polymerize, low yields of said acid chloride are obtained in the known processes. In the reaction of phosgene with α-chloroacrylic acid in the presence of dimethyl formamide, the yield of the crude product is in the range of from 75 to 85%, but the distillate contains only from 50 to 70% of α-chloroacrylic acid chloride (see comparative example 1).

It is of special note that the dehydrochlorination of α,β-dichloropropionic acid chloride with diethyl aniline, as disclosed in *J. Am. Chem. Soc.*, Vol. 62, at 3495 (1940), is likely to result in the polymerization of a great part of the final product in the reaction mixture.

When using dimethyl formamide in the hydrogen chloride separation from α,β-dichloropropionic acid chloride, the unsaturated acid chloride is obtained in a yield of from, 55 to 65%, but it is disadvantageous that uncontrollable polymerizations often occur in the reaction mixture, especially in the case of large charges.

The cited processes all have in common that unsatisfactory yields and purities of the desired reaction product are obtained. However, the purity of the α-chloroacrylic acid chloride obtained is of decisive importance for its further use, for example, as a monomer for polymerizations, because the very sensitive acid chloride may only be further purified with considerable loss, especially due to polymerization.

A process has now been found for preparing α-chloroacrylic acid chloride by dehydrochlorination of α,β-dichloropropionic acid chloride in the presence of certain nitrogen and phosphorus compounds, which comprises carrying out the reaction at a temperature of from 60° to 120° C and at a pressure below 200 torrs (1 torr = 1 mm of Hg).

The above-mentioned nitrogen and phosphorus compounds are more specifically tertiary amines, quaternary ammonium salts, tertiary phosphines, quaternary phosphonium salts and tertiary phosphine oxides, sulfides, halides and imines.

The dehydrochlorination of α-chloroacrylic acid chloride in the presence of the above-mentioned phosphorus compounds is particularly advantageous because it has now been discovered that the uncontrollable polymerization of the final product in the reaction mixture is eliminated when said phosphorus compounds are present, whereas such polymerization is not always eliminated during the above-identified dehydrochlorination when said nitrogen compounds are present. This same elimination of polymerization is an unexpected advantage of the above-identified dehydrochlorination in the presence of said phosphorus compounds over the process described in the above-mentioned *J. Am. Chem. Soc.* publication.

Thus, this invention relates to a process for preparing α-chloroacrylic acid chloride by dehydrochlorinating α,β-dichloropriopinic acid chloride at a temperature of from 60° to 120° C and a pressure of below 200 mm of Hg in the presence of a tertiary phosphine of the formula

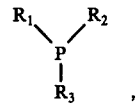

a quaternary phosphonium salt of the formula

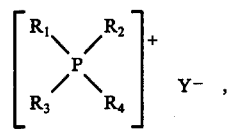

a tertiary phosphine oxide, sulfide or imine of the formula

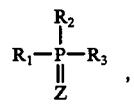

or a tertiary phosphine halide of the formula

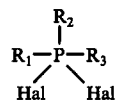

$R_1$, $R_2$ and $R_3$ each is alkyl of from 1 to 20 carbon atoms, preferably 1 to 12 carbon atoms and especially 1 to 4 carbon atoms; cycloalkyl of from 4 to 8 carbon atoms, preferably 5 to 6 carbon atoms; phenyl; phenalkyl of from 7 to 20 carbon atoms, preferably 7 or 8 carbon atoms; said alkyl, cycloalkyl, phenyl or phenalkyl which is substituted, preferably by one halogen, especially chlorine or bromine, or by one dialkylamino, each dialkylamino-alkyl being of from 1 to 4 carbon atoms; or

R' and R" each being alkyl of 1 to 20 carbon atoms, phenyl, phenalkyl of 7 to 20 carbon atoms, or said alkyl, phenyl or phenalkyl which is substituted, preferably by one halogen, especially chlorine or bromine, or by one dialkylamino, each dialkylamino-alkyl being of from 1 to 4 carbon atoms.

$R_4$ is hydrogen; alkyl of from 1 to 20 carbon atoms, preferably 1 to 12 carbon atoms and especially 1 to 4 carbon atoms; cycloalkyl of from 4 to 8 carbon atoms, preferably 5 or 6 carbon atoms; phenyl, phenalkyl of from 7 to 20 carbon atoms; preferably 7 or 8 carbon atoms; or said alkyl, cycloalkyl, phenyl or phenalkyl substituted, preferably by one halogen, especially chlorine or bromine, or by one dialkylamino, each dialkylamino-alkyl being of from 1 to 4 carbon atoms.

Y is a radical of an organic or inorganic acid, for example, a halogen, a sulfate, a methylsulfate, or the radical of an organic sulfonic acid.

Z is oxygen; sulfur; or $NR_5$, $R_5$ being alkyl of 1 to 20 carbon atoms, preferably 1 to 12 carbon atoms and especially 1 to 4 carbon atoms, cycloalkyl of 4 to 8 carbon atoms, preferably 5 or 6 carbon atoms, phenyl, phenalkyl of from 7 to 20 carbon atoms, preferably 7 or 8 carbon atoms, or said alkyl, cycloalkyl, phenyl, or phenalkyl substituted preferably by one halogen, especially chlorine or bromine, or by one dialkylamino, each dialkylamino-alkyl being of from 1 to 4 carbon atoms.

Hal is a halogen, preferably chlorine.

Any two of $R_1$ to $R_5$ may together form an aliphatic chain or such chain interrupted by nitrogen, oxygen or sulfur.

The catalytic compounds may contain a number of the same or different constituents selected from the group consisting of oxygen, sulfur, halogen or $NR_5$. The molecular weight of the catalyst used is preferably up to 500, especially up to 200.

Examples of catalysts to be used according to the invention are:

tertiary phosphines such as trimethyl phosphine, triethyl phosphine, tripropyl phosphine, tributyl phosphine, triphenyl phosphine, methyldiethyl phosphine, dimethylpropyl phosphine, and diethylbenzyl phosphine; quaternary phosphonium salts such as tetraethyl phosphonium chloride, trimethyl benzyl phosphonium chloride, and triphenyl ethyl phosphonium benzene sulfonate;

organic compounds of 5-valent phosphorus such as trimethyl phosphine oxide, tributyl phosphine oxide, trihexyl phosphine oxide, triphenyl phosphine oxide, dimethyl phenyl phosphine oxide, dimethyl chloromethyl phosphine oxide, dimethyl hexyl phosphine oxide, dimethyl dodecyl phosphine oxide, dimethyl eicosyl phosphine oxide, dimethyl phenyl phosphine sulfide, dimethyl dodecyl phosphine sulfide, 2-dimethyl-phosphinyl-propionic-acid-methyl-ester (the phosphorus atom is substituted by 3-methyl-3-oxo-propyl), 1-methyl-phospholene-3 ($R_1$ and $R_2$ together are 2-butenyl), and 1-ethyl-3-methyl-phospholene-3 ($R_1$ and $R_2$ together 2-methyl-2-butenyl).

Preferred catalysts are tertiary phosphine oxides, wherein $R_1$, $R_2$ and $R_3$ each is an alkyl group of from 1 to 20 carbon atoms, preferably 1 to 4 carbon atoms, or a phenyl group.

In the hydrogen chloride cleavage according to the invention the catalyst is used in an amount from 0.5 to 5% by weight, preferably from 1 to 3% by weight, calculated on the $\alpha,\beta$-dichloropropionic acid chloride used. The catalysts may be added as such or in the form of their salts, preferably in the form of their hydrochlorides.

The cleavage temperature is in the range of from 60° to 120° C. Higher temperatures can be used, but may cause losses. The preferred temperature range is from 70° to 100° C.

Owing to its thermal instability, the $\alpha$-chloroacrylic acid chloride is advantageously distilled off from the reaction chamber in the same measure as it is formed under reduced pressure, generally below 200 torrs, preferably below 100 torrs and above 40 torrs, for example from 50 to 80 torrs.

In order to obtain a product as pure as possible, the gas mixture leaving the reaction chamber is advantageously passed into the reflux condenser, the temperature of which, depending on the pressure used, is maintained such that unreacted $\alpha,\beta$-dichloropropionic acid chloride completely condenses and refluxes into the reaction zone. The temperature of the condenser is in the range of from 0° to 50° C depending on the pressure, advantageously from 20° to 40° C.

It is especially advantageous to pass the refluxing product into a fractionating attachment charged with filling bodies, especially copper or copper-plated bodies, for the purpose of fractionating it.

The portions passing through the reflux condenser, consisting essentially of hydrogen chloride and $\alpha$-chloroacrylic acid chloride, are worked up in known manner, especially by completely condensing the $\alpha$-chloroacrylic acid chloride formed at low temperatures. The obtained product is very pure and may generally be used directly, for example for prostaglandin syntheses. The process according to the invention consequently has a considerable technical advantage.

The following examples illustrate the invention.

COMPARATIVE EXAMPLE 1 (ACCORDING TO GERMAN PAT. NO. 1,167,819)

106.5 g of phosgene were introduced at 40° C into a mixture of 106.5 g of $\alpha$-chloroacrylic acid and 11.7 g of dimethyl formamide for a period of 3 hours. Thereafter the reaction product was split off under a pressure of from 60 to 70 torrs (temperature of the bath 115° to 150° C), the chloroacrylic acid chloride formed was then distilled off, condensed in a brine condenser (−20° to −30° C) and collected in a receiver cooled with isopropanol/dry ice. The yield of the crude product in this process was in the range of from 75 to 85%. The content of $\alpha$-chloroacrylic acid chloride in the distillate varies from 50 to 70% according to gas chromatographic analyses.

EXAMPLES 1 to 11:

400 g of $\alpha,\beta$-dichloropropionic acid chloride and 2% by weight of each of the catalysts indicated in the following table were slowly heated under reduced pressure of from 60 to 70 torrs to a temperature of from 60° to 90° C. The $\alpha$-chloroacrylic acid chloride formed distilled in this process over a column filled with copper spirals and superposed by a short reflux condenser charged with water at a temperature of from 30° to 35° C. It was then condensed in a brine condenser (−20° to −30° C) and collected in a receiver cooled with isopropanol/dry ice. The resulting yields of α-chloroacrylic acid chloride as well as their purity, as determined by gas chromatography, are summarized in the following table.

TABLE 1

| Example | Catalyst | Yield in % of the theory | Purity (determined by gas chromatography) | | | |
|---|---|---|---|---|---|---|
| | | | Cl₂C=COCl (%) | | Cl₂CH-COCl (%) | Further products (%) |
| 1 | (CH₃)₃PO | 95 | 98.5 | | 1.3 | 0.2 |
| 2 | (C₆H₅)₃PO | 90 | 94.4 | | 5.6 | — |
| 3 | (C₆H₁₃)PO(CH₃)₂ | 71 | 99.0 | | — | 1.0 |
| 4 | (C₆H₅)PO(CH₃)₂ | 67 | 99.5 | | 0.3 | 0.2 |
| 5 | (C₈H₁₇)PO(CH₃)₂ | 83 | 99.5 | | 0.3 | 0.2 |
| 6 | (C₁₀H₂₁)PO(CH₃)₂ | 89 | 98.7 | | 1.2 | 0.1 |
| 7 | (C₁₂H₂₅)PO(CH₃)₂ | 98 | 97.8 | | 1.8 | 0.4 |
| 8 | (C₁₆H₃₃)PO(CH₃)₂ | 93.5 | 95.9 | | 3.9 | 0.2 |
| 9 | 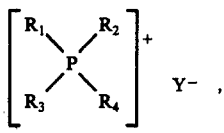 | 91 | 98.3 | | 1.4 | 0.3 |
| 10 | (C₆H₅)₃P | 90 | 99.9 | | — | 0.1 |
| 11 | [(CH₃)₂N]₃PO | 98 | 96.5 | | 3.5 | — |

We claim:
1. A process for preparing α-chloroacrylic acid chloride by dehydrochlorinating α,β-dichloropropionic acid chloride at a temperature of from 60° to 120° C and a pressure of below 200 mm of Hg in the presence of a tertiary phosphine of the formula

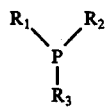

a quaternary phosphonium salt of the formula

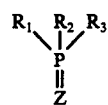

a tertiary phosphine oxide, sulfide or imine of the formula

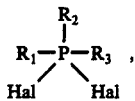

or a tertiary phosphine halide of the formula $$\begin{array}{c} R_2 \\ | \\ R_1-P-R_3 \\ / \quad \backslash \\ Hal \quad Hal \end{array}$$

wherein $R_1$, $R_2$ and $R_3$ each is alkyl of from 1 to 20 carbon atoms; cycloalkyl of from 4 to 8 carbon atoms; phenyl; phenalkyl of from 7 to 20 carbon atoms; said alkyl, cycloalkyl, phenyl or phenalkyl which is substituted;

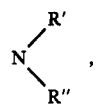

R' and R" each being alkyl of from 1 to 20 carbon atoms, phenyl, phenalkyl of from 7 to 20 carbon atoms, or said alkyl, phenyl or phenalkyl which is substituted; wherein $R_4$ is hydrogen; alkyl of from 1 to 20 carbon atoms; cycloalkyl of from 4 to 8 carbon atoms; phenyl; phenalkyl of from 7 to 20 carbon atoms; or said alkyl, cycloalkyl, phenyl or phenalkyl which is substituted; wherein Y is a radical of an organic or inorganic acid; wherein Z is oxygen, sulfur, or $NR_5$, $R_5$ being alkyl of from 1 to 20 carbon atoms, cycloalkyl of from 4 to 8 carbon atoms, phenyl, phenalkyl of from 7 to 20 carbon atoms, or said alkyl, cycloalkyl, phenyl or phenalkyl which is substituted; wherein Hal is halogen; and wherein any two of $R_1$, $R_2$, $R_3$, $R_4$, and $R_5$ may together form an aliphatic chain or said chain interrupted by nitrogen, oxygen or sulfur.

2. The process as defined in claim 1, wherein $R_1$, $R_2$ and $R_3$ each is alkyl of from 1 to 20 carbon atoms; phenyl; phenalkyl of from 7 to 20 carbon atoms; or

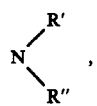

R' and R" each being alkyl of from 1 to 20 carbon atoms, phenyl, or phenalkyl of from 7 to 20 carbon atoms; or wherein $R_1$ and $R_2$ together form an aliphatic chain of 4 to 5 carbon atoms; wherein $R_4$ is hydrogen, alkyl of from 1 to 20 carbon atoms, phenyl, or phenalkyl of from 7 to 20 carbon atoms; and wherein Z is oxygen, sulfur or $NR_5$, $R_5$ being alkyl of 1 to 20 carbon atoms, phenyl or phenalkyl of 7 to 20 carbon atoms.

3. The process defined in claim 1, wherein dehydrochlorination occurs in the presence of a tertiary phosphine and $R_1$, $R_2$ and $R_3$ each is alkyl of from 1 to 20 carbon atoms, phenyl, or phenalkyl of from 7 to 20 carbon atoms.

4. The process as defined in claim 1, wherein dehydrochlorination occurs in the presence of a quaternary phosphonium salt and $R_1$, $R_2$, $R_3$ and $R_4$ each is alkyl of from 1 to 20 carbon atoms, phenyl or phenalkyl of from 7 to 20 carbon atoms and Y is halogen or the radical of an organic sulfonic acid.

5. The process as defined in claim 1, wherein dehydrochlorination occurs in the presence of a tertiary phosphine oxide and $R_1$, $R_2$ and $R_3$ each is alkyl of from 1 to 20 carbon atoms, haloalkyl of from 1 to 20 carbon atoms, phenyl, phenalkyl of from 7 to 20 carbon atoms,

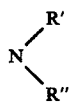

R' and R''each being alkyl of from 1 to 20 carbon atoms, or wherein $R_1$ and $R_2$ together are 2-butenyl.

6. The process as defined in claim 5, wherein the catalyst is a tertiary phosphine oxide and $R_1$, $R_2$, and $R_3$ each is alkyl of from 1 to 20 carbon atoms or phenyl.

7. The process as defined in claim 6, wherein the catalyst is trimethyl phosphine oxide.

8. The process as defined in claim 6, wherein the catalyst is dimethyl phenyl phosphine oxide.

9. The process as defined in claim 6, wherein the catalyst is dimethyl octyl phosphine oxide.

10. The process as defined in claim 6, wherein the catalyst is dimethyl dodecyl phosphine oxide.

11. The process defined in claim 1, wherein the dehydrochlorination occurs in the presence of a tertiary phosphine sulfide wherein $R_1$, $R_2$, and $R_3$ each is alkyl of from 1 to 20 carbon atoms or phenyl.

12. The process as defined in claim 1, wherein the catalyst is present in an amount of from 0.5 to 5% by weight, calculated on the $\alpha,\beta$-dichloropropionic acid chloride.

13. The process as defined in claim 8, wherein the catalyst is present in an amount of from 1 to 3% by weight.

14. A process for preparing $\alpha$-chloroacrylic acid chloride by dehydrochlorinating $\alpha,\beta$-dichloropropionic acid chloride at a temperature of from 60° to 120° C and a pressure of below 200 mm of Hg in the presence of 2-dimethyl-phosphinyl propionic-acid-methyl-ester.

15. A process for preparing $\alpha$-chloroacrylic acid chloride by dehydrochlorinating $\alpha,\beta$-dichloropropionic acid chloride at a temperature of from 60° to 120° C and a pressure of below 200 mm of Hg in the presence of 1-ethyl-3-methylphospholene-3.

16. A process for preparing $\alpha$-chloroacrylic acid chloride by dehydrochlorinating $\alpha,\beta$-dichloropropionic acid chloride at a temperature of from 60° to 120° C and a pressure of below 200 mm of Hg in the presence of triphenyl-ethylphosphonium-benzene-sulfonate.

* * * * *

UNITED STATES PATENT AND TRADEMARK OFFICE
CERTIFICATE OF CORRECTION

PATENT NO. : 4,066,690
DATED : January 3, 1978
INVENTOR(S) : Reuschling et al.

It is certified that error appears in the above-identified patent and that said Letters Patent are hereby corrected as shown below:

In the Heading, Item [30], change "July 24, 1975" to

--Nov. 19, 1973--.

*Signed and Sealed this*

*Eighteenth* Day of *April 1978*

[SEAL]

Attest:

RUTH C. MASON
*Attesting Officer*

LUTRELLE F. PARKER
*Acting Commissioner of Patents and Trademarks*